(12) United States Patent
Gröger et al.

(10) Patent No.: US 7,939,301 B2
(45) Date of Patent: May 10, 2011

(54) ENZYME REACTIONS IN MINIEMULSIONS

(75) Inventors: Harald Gröger, Hanau (DE); Karlheinz Drauz, Freigericht (DE); Hendrik Hüsken, Haltern am See (DE); Katharina Landfester, Ulm (DE)

(73) Assignee: Evonik Degussa GmbH, Essen (DE)

( * ) Notice: Subject to any disclaimer, the term of this patent is extended or adjusted under 35 U.S.C. 154(b) by 789 days.

(21) Appl. No.: 11/802,798

(22) PCT Filed: Nov. 4, 2005

(86) PCT No.: PCT/EP2005/011824
§ 371 (c)(1),
(2), (4) Date: Aug. 29, 2007

(87) PCT Pub. No.: WO2006/058595
PCT Pub. Date: Jun. 8, 2006

(65) Prior Publication Data
US 2008/0020423 A1 Jan. 24, 2008

(30) Foreign Application Priority Data
Nov. 30, 2004 (DE) .......... 10 2004 057 966

(51) Int. Cl.
C12P 13/04 (2006.01)
C12P 21/02 (2006.01)
C12N 9/02 (2006.01)
C12N 9/10 (2006.01)

(52) U.S. Cl. .......... 435/106; 435/41; 435/183; 435/189; 435/193; 435/195; 435/232; 435/233; 435/252.33

(58) Field of Classification Search .......... None
See application file for complete search history.

(56) References Cited

U.S. PATENT DOCUMENTS

| | | |
|---|---|---|
| 6,713,288 B1 | 3/2004 | Altenbuchner |
| 2003/0175910 A1 | 9/2003 | Altenbuchner |

FOREIGN PATENT DOCUMENTS
WO WO-2004/035801 4/2004

OTHER PUBLICATIONS

International Preliminary Report on Patentability for PCT/EP2005/011824 filed Nov. 4, 2005.
International Search Report for PCT/EP2005/011824, Pub Date Feb 20, 2006.
Written Opinion of the International Searching Authority for PCT/EP2005/011824, Pub Date Apr. 18, 2007.
De Jesus, et al., "Enzymatic Resolution of Alcohols Via Lipases Immobilized in Microemulsion-Based Gels," *Tetrahedron: Asymmetry* 6:63-66 (1995).
Gröger, et al., "The First Aminoacylase-Catalyzed Enantioselective Synthesis of Aromatic β-Amino Acids," *Org. Biomol. Chem.* 2:1977-1978 (Jan. 2004).
Landfester, et al., "Enzymatic Polymerization Towards Biodegradable Polyester Nanoparticles," *Macromol. Rapid Commun.* 24:512-516 (2003).
Moon, et al., "Application of Ultrasound to Organic Reactions: Ultrasonic Catalysis on Hydrolysis of Carboxylic Acids Esters," *Tetrahedron Letters* 41:3917-3920 (1979).
Taden, et al., "Enzymatic Polymerization Towards Biodegradable Polyester Nanoparticles," *Macromol. Rapid Commun.* 24:512-516 (2003).
Yim, et al., "Ultrasonic Enhancement on the Hydrolysis of Diethyl 1,2-Benzenedicarboxylate," *Chemistry Letters* p. 938 (2001).
Zheng, et al., "Seperation of Enantiomers in Microemulsion Electrokinetic Chromatography Using Chiral Alcohols as Cosufactants," *Electrophoresis* 25:3263-3269 (2004).
Gröger, Harald, "Enantioselective biocatalysis in nanoscale-reactors: Mini-emulsions as reaction media for enzymatic resolution," Biocatalysis Workshop, Session 6, Apr. 14, 2005; Manchester England, XP-002365943.
English language abstract for WO-2004/035801, Pub Date Apr. 29, 2004.

*Primary Examiner* — Herbert J. Lilling
(74) *Attorney, Agent, or Firm* — Law Office of: Michael A. Sanzo, LLC

(57) ABSTRACT

The present invention is directed towards an asymmetric enzymic process for preparing optically active organic compounds. The process according to the invention is carried out in what are termed miniemulsions. The invention also relates to an enzymic reaction mixture which exhibits a miniemulsion.

18 Claims, 1 Drawing Sheet

ENZYME REACTIONS IN MINIEMULSIONS

CROSS REFERENCE TO RELATED APPLICATIONS

The present application represents U.S. national stage of international application PCT/EP2005/011824, which had an international filing date of Nov. 4, 2005, and which was published in English under PCT Article 21(2) on Jun. 8, 2006. The international application claims priority to German application 10 2004 057 966.0, filed on Nov. 30, 2004. These prior applications are incorporated in their entirety herein by reference.

FIELD OF THE INVENTION

The present invention is directed towards a process for preparing optically active organic compounds. A characteristic feature of the optically active organic compounds which are to be prepared is that they are obtained asymmetrically by way of one or more stereoselective enzymic transformations. These latter take place in what is termed a miniemulsion. The present invention also relates to a reaction system in which such a reaction can take place preferentially.

BACKGROUND OF THE INVENTION

Enzymic procedural steps are also increasingly being used in industrial processes for preparing organic compounds. This is due, inter alia, to the fact that the enzymes which are employed as biocatalysts already display an appropriate industrial effect in small quantities, the catalysis can in principle take place under mild reaction conditions (temperature, pressure and pH) and, at the same time, the enzymic transformation is associated with a high degree of enantioselectivity, regioselectivity or chemoselectivity. For this reason, efforts are still being made to improve these conversion reactions, and make them utilizable in an industrial process, with a view to exploiting these advantages in as broad a context as possible.

In this connection, the possibility of industrially preparing organic compounds by way of asymmetric enzymic transformations is being investigated in detail. In this context, it can frequently be found that disadvantages emerge with regard to using enzymes in large industrial dimensions, which disadvantages, such as excessive solvent use and solubility or material transport problems, call into question the use of the enzymes for these purposes. In this connection, the implementation of biocatalytic reactions using high substrate concentrations is particularly challenging.

Landfester et al. describe the enzymic polymerization of lactones in systems which exhibit a continuous aqueous phase in which a discontinuous hydrophobic phase is distributed in what are termed miniemulsion droplets. This miniemulsion is obtained, inter alia, by the action of ultrasound or high pressure homogenizers on a mixture which possesses these two phases. In addition, hydrophobic auxiliary substances and surfactants are present in the mixture for the purpose of stabilizing the droplets (Macromol. Rapid Commun. 2003, 24, 512-516; DE10248455).

SUMMARY OF THE INVENTION

The object of the present invention was to specify a process for preparing optically active organic compounds using asymmetric enzymic reaction steps. In particular, this process was to be superior to the processes of the prior art in regard to efficiency with, however, the advantages, which were mentioned at the outset, of the enzymic transformations still being present.

The set object is surprisingly and very advantageously achieved by carrying out a process for the asymmetric enzymic preparation of optically active organic compounds, in particular low molecular weight, nonpolymeric, chiral molecules, in miniemulsions. Using the miniemulsions also makes it possible to allow enzymic transformations which proceed asymmetrically to take place in a manner which is superior to, in particular more efficient than, the prior art. Thus, it is possible either to reduce the reaction time by using the same quantity of enzyme to be employed or to increase the utilizable quantity of organic compounds to be converted as compared with the previously known processes, with this in both cases helping to bring about a higher space/time yield.

DESCRIPTION OF THE INVENTION

Figure 1:
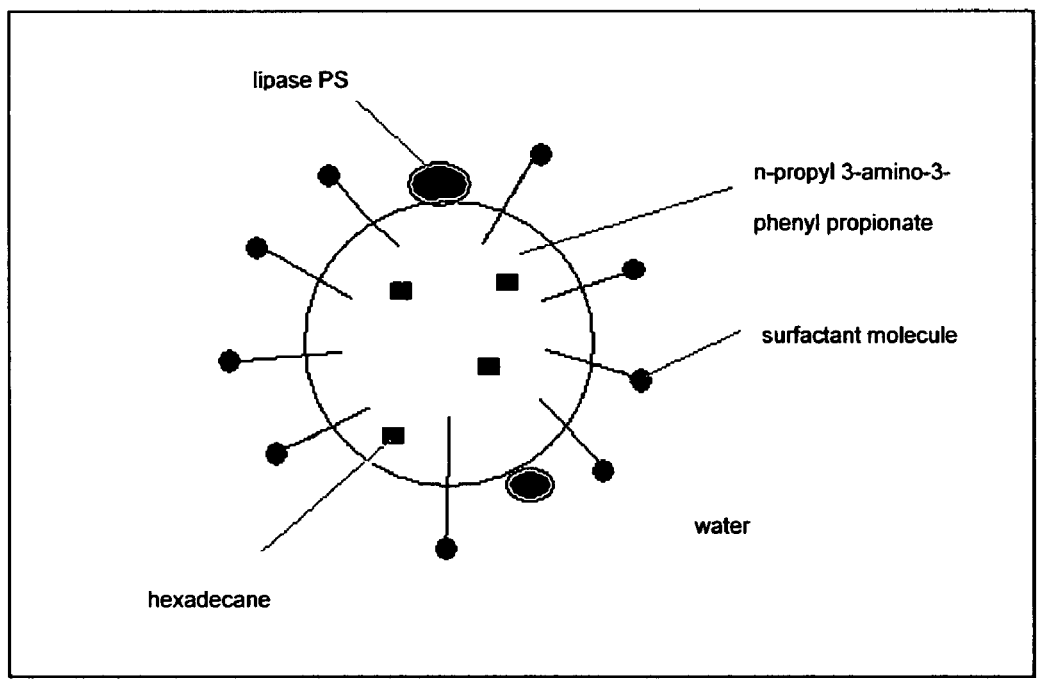
FIG. 1: A diagram of droplets of a miniemulsion is shown in the FIGURE.

In accordance with the invention, a miniemulsion is understood as being a mixture in which small stable droplets, which are obtained by the intensive use of shearing forces, in particular ultrasound, a steel disperser or microfluidizer, are present in dispersed form, preferably over the duration of the reaction in question, in a second continuous phase.

Advantageously, droplets having a hydrophobic character are generated in an aqueous medium. In accordance with the invention, an aqueous medium is understood as being a homogeneous phase in which water forms the main constituent. However, other organic solvents which are soluble in water, e.g. alcohols such as methanol, ethanol, n-propanol, isopropanol, sec-isobutanol, tert-isobutanol, glycerol and glycol, or ketones, in particular acetone and MIBK, or DMSO, DMF, NMP or sulfolane, can also be admixed with this phase.

Any liquids which the skilled person takes into consideration for this purpose can be employed as the hydrophobic phase. When selecting the liquid, the skilled person bases himself, in the first place, on whether this liquid forms a two-phase mixture with water under the given reaction conditions and whether it reacts inertly towards the enzymic transformation.

Where appropriate, the addition of such a hydrophobic liquid can be dispensed with when the substrate to be employed is liquid and can itself assume the function of the hydrophobic phase. This differs from substrate to substrate and must be verified by the skilled person in each individual case. If it is necessary to add a further hydrophobic liquid (phase) in addition to the substrate, for example because the latter is a solid, the skilled person will then select, for this purpose, a liquid which is preferably from the group consisting of ethers, esters and hydrocarbons. Very particular preference is given to using MTBE, ethyl acetate, n-hexane, n-heptane, cyclohexane and toluene.

In this connection, the drops can, for example, be distributed by treating the mixture with ultrasound, a steel disperser or a microfluidizer (K. Landfester, M. Antonietti, "Miniemulsions the convenient synthesis of organic and inorganic nanoparticles and "single molecule" applications in materials chemistry" in: Colloids and Colloid Assemblies (Ed.: F. Caruso), Wiley VCH Verlag, Weinheim, Germany, 2004, pp. 175-215 and the literature which is cited therein). The miniemulsion droplets preferably exhibit a mean droplet diameter of from 20 to 1000 nanometers, in particular of from 30 to 600 nanometers and very particularly preferably of from 50 to 500 nanometers.

For preparing the miniemulsions, it is advantageous to add a surfactant to the mixture before generating the droplets. The surfactant is preferably employed in a range of from 1 to 20% by weight, more preferably of from 2 to 15% by weight, and very preferably between 3 and 10% by weight, based on the quantity of emulsion. In principle, any surfactants which the skilled person takes into consideration for this purpose and which do not inactivate the enzymes to be employed are suitable for the described use. However, it is advantageous to use what are termed nonionic surfactants as described, for example, in A. Taden, M. Antonietti, K. Landfester, Macromol. Rapid Commun. 2003, 24, 512-516. Very particular preference is given to using surfactants which are selected from the group consisting of ethoxylates of alkyl polyethylene glykol ethers, in particular "LUTENSOL" AT, very particular "LUTENSOL" AT 50 ($C_{16/18}$-$EO_{8\ to\ 50}$).

In addition, the emulsion droplets which are formed are stabilized by adding further inert substances which are as a rule hydrophobic. A prerequisite is that these substances exhibit a lower solubility in water than the hydrophobic phase. Suitable substances of this nature are, in particular, aliphatic or aromatic hydrocarbons. The aliphatic hydrocarbons which are preferred are, in particular, the $C_6$-$C_{20}$-alkanes. These are very particularly preferably selected from the group of hydrocarbons which consist, in particular, of hexadecane. These hydrophobic substances are preferably employed in a quantity, based on the miniemulsion of between 0.001 and 70% by weight, preferably 0.1 and 3% by weight and particularly preferably of between 0.5 and 2% by weight.

The enzymes which are enlisted for asymmetrically preparing optically active organic compounds can be selected by the skilled person in an appropriate manner. In principle, the present process can be applied to any enzymes which the skilled person takes into consideration for this purpose. Enzymes selected from the group of oxidoreductases, hydrolases, isomerases, transferases and lyases have been found to be advantageously employable. Very particular preference is given to using lipases and oxidoreductases. Extreme preference is given to using the Lipase PS from the Amano company.

The enzymes can advantageously be taken from the following organisms: Arthobacter strains, in particular *Arthobacter paraffineus*, *Aspergillus* strains, in particular *Aspergillus niger*, *Bacillus* strains, in particular *Bacillus subtilis*, *Bacillus cereus* and *Bacillus stearothermophilus*, *Burkholderia* strains, in particular *Burkholderia cepacia*, *Candida* strains, in particular *Candida antarctica*, *Candida boidinii* and *Candida rugosa*, *Lactobacillus* strains, in particular *Lactobacillus kefir* and *Lactobacillus brevis*, *Mucor* strains, in particular *Mucor javanicus*, *Penicillium* strains, in particular *Penicillium camemberti*, *Pseudomonas* strains, in particular *Pseudomonas cepacia* and *Pseudomonas fluorescens*, *Rhizopus* strains, in particular *Rhizopus oryzae*, *Rhodococcus* strains, in particular *Rhodococcus erythropolis*, *Rhodococcus ruber* and *Rhodococcus rhodocrous*, and also *Thermoplasma acidophilum*.

In principle, any compounds which spring to the mind of the skilled person for reacting with enzymes can be enlisted as substrates. The substrates are preferably of a solid or liquid nature and possess no, or at least one, chiral centre. The products which are generated in the present reaction arise in an optically enriched form, i.e. meaning that one enantiomer out of a mixture of two possible enantiomers, or proceeding from a prochiral compound, is formed preferentially. The enantiomeric excess which is generated in the product is preferably >80%, more preferably >90%, even more preferably >95% and very preferably >98%. Substance classes which are preferably employed in the reaction according to the invention can be selected, for example, from the group consisting of racemic α- or β-amino acid esters, α- or β-hydroxycarboxylic acid esters and prochiral ketones. Very great preference is given to using racemic β-amino acid esters, in particular n-propyl rac-3-amino-3-phenylpropionates, as substrate.

The present enzymic reaction can preferably be carried out at relatively high substrate concentrations. Preference is given to using starting quantities of substrate of >300 g/l, in particular >450 g/l and very particularly preferably >600 g/l for the enzymic transformations in miniemulsions.

The enzyme or enzymes which is/are involved in the preparation of the optically active organic compound can be employed in the reaction in question as such or in the form of a microorganism which exhibits one or more of these enzymes. In accordance with the invention, the expression "as such" is to be understood as meaning that the enzymes are added to the miniemulsion as native or recombinantly prepared proteins which are in as highly a purified form as desired. In principle, however, it is also possible to use one or more of the enzymes as constituents of a microorganism. The microorganism is accordingly a cell in which at least one gene is expressed, that is to say at least one protein which can catalyze the transformation according to the invention is present. If the gene is present in recombinant form in the microorganism, the microorganism is then referred to as being a host organism. The host organism can contain the gene in integrated form in the chromosome or on a plasmid. If several enzymes are involved in the enzymic transformation and expressed together in recombinant form by a host organism, the latter is then referred to, in this present case, as being a whole cell catalyst.

When several enzymes are being used as such or in the form of a whole cell catalyst, for example in a reaction cascade, it is then sufficient, in accordance with the invention, for at least one enzyme to bring about an asymmetric transformation of the corresponding substrate (EP1216304—in this case hydantoin racemase/hydantoinase/stereoselective carbamoylase).

Host organisms which may be mentioned in this regard are organisms such as yeasts, such as *Hansenula polymorpha, Pichia* sp. and *Saccharomyces cerevisiae*, prokaryotes, such as *E. coli* and *Bacillus subtilis*, or eukaryotes, such as mammalian cells, insect cells or plant cells. The methods for cloning are well known to the skilled person (Sambrook, J.; Fritsch, E. F. and Maniatis, T. (1989), Molecular cloning: a laboratory manual, $2^{nd}$ ed., Cold Spring Harbor Laboratory Press, New York). Preference is given to using *E. coli* strains for this purpose. Those which are very particularly preferred are: *E. coli* XL1 Blue, NM 522, JM101, JM109, JM105, RR1, DH5α, TOP 10-, HB101, BL21 codon plus, BL21 (DE3) codon plus, BL21, BL21 (DE3) and MM294.

In principle, any embodiments which are available to the skilled person for this purpose are suitable for use as plasmids or vectors for cloning the genes in question. These plasmids and vectors can be found, for example, in Studier and coworkers (Studier, W. F.; Rosenberg A. H.; Dunn J. J.; Dubendroff J. W.; (1990), Use of the T7 RNA polymerase to direct expression of cloned genes, Methods Enzymol. 185, 61-89) or the brochures provided by the companies Novagen, Promega, New England Biolabs, Clontech or Gibco BRL. Other preferred plasmids and vectors can be found in: Glover, D. M. (1985), DNA cloning: a practical approach, Vol. I-III, IRL Press Ltd., Oxford; Rodriguez, R. L. und Denhardt, D. T (eds) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, $2^{nd}$ ed., Cold Spring Harbor Laboratory Press, New York.

Plasmids which can be used to clone the gene constructs containing the nucleic acid sequences under consideration into the host organism in a very preferred manner are, or are based on: pUC18/19 (Roche Biochemicals), pKK-177-3H (Roche Biochemicals), pBTac2 (Roche Biochemicals), pKK223-3 (Amersham Pharmacia Biotech), pKK-233-3 (Stratagene) or pET (Novagen).

It has proven to be advantageous, when carrying out the process according to the invention, for the microorganism or host organism to be pretreated, preferably before being used, such that the permeability of its cell membrane for the substrates and products is increased as compared with the intact system. In this connection, particular preference is given to a process in which the microorganism or host organism is, for example, pretreated by being frozen and/or treated with an organic solvent, in particular toluene.

In another embodiment, the present invention deals with a reaction mixture which exhibits a miniemulsion which comprises a continuous aqueous phase and a hydrophobic discontinuous phase, a stereoselective enzyme which is involved in the asymmetric preparation of the organic compound or a microorganism which contains this enzyme, a surfactant, a hydrophobic substance which stabilizes the emulsion droplets and a prochiral or racemic or enantiomerically enriched organic compound which is to be converted by the enzyme, and/or the reaction product of this compound. The preferred embodiments of the process according to the invention are valid here by analogy.

The reader is referred to the prior art which was cited at the outset with regard to generating a reaction mixture according to the invention in the form of a miniemulsion. The preparation variants which are specified in that prior art can be applied in a corresponding manner to the present invention.

Thus, a miniemulsion can be formed, for example, by means of subjecting a mixture composed of organic solvents and an aqueous phase to ultrasound treatment. This gives rise to a homogeneous, milky liquid which, under the given conditions and with the addition of the described additives, no longer demixes during the period of the enzymic transformations and is therefore consequently stable within the meaning of the invention. The settings for the other reaction parameters such as pH or temperature depend on the underlying enzymic transformation and can be ascertained by the skilled person by means of routine experiments.

Thus, for example, a surfactant-containing and hexadecane-containing aqueous mixture which comprises n-propyl 3-amino-3-phenyl propionate can be converted into a miniemulsion by means of ultrasound. A diagram of the droplets obtained when using a lipase is shown in FIG. 1. In this connection, the lipase can be added prior to the ultrasound treatment or be stirred into the miniemulsion after the ultrasound treatment. The product of the enzymic transformation, in this case (S)-3-amino-3-phenyl-n-propionic acid, precipitates out from this miniemulsion during the reaction and can be separated off from the remainder of the reaction mixture by means of simple filtration. When the miniemulsion was used, the reaction rate was found to be increased as compared with that of the previous procedure (see Example 1 (comparative example) and Example 2). Surprisingly, the formation of a solid during the reaction does not lead to the miniemulsion becoming unstable even though solids can destabilize miniemulsions.

Consequently, the miniemulsion also remains stable despite the ongoing formation of the third phase, namely the solid phase, something which was not to be expected. It is furthermore surprising that the solids which are formed have a particle diameter which is suitable for (industrial) filtrations. This was not to be expected since, by definition, the miniemulsion is composed of very small spatially separated droplets which should then, because of the resulting increase, specifically as compared with standard precipitation processes, in the number of crystallization nuclei, lead to a finely divided solid having a small particle diameter, with this in turn leading to corresponding difficulties in connection with filtration.

It was furthermore also surprising that it was possible, as a result of using the miniemulsion, to increase the substrate concentration while at the same time retaining the stirring properties and achieving high turnovers. The experiments were carried out using substrate concentrations of several hundred grams per liter, e.g. 482 g/l (see Example 3). This is one of the highest substrate concentrations for enzymic enantioselective reactions that has at all been reported to date. For a long time now, it has been known to use ultrasound in the hydrolysis of carboxylic esters (Yim et al., Chemistry Letters 2001, p. 938; Moon et al. Tetrahedron Letters 1979, 41, 3917). It is reported that using ultrasound can increase the hydrolysis of the esters. In this case, it is surprising that, in the reaction which has just been described, a symmetrical cleavage of the esters, with the formation of an undesirable racemate instead of the desired optically active product, does not occur as a result of using ultrasound and that in fact it is only the enzymic asymmetric hydrolysis which is prominent, with this being made clear by the very good ee values of the product. The actual, undesirable, symmetrical hydrolysis which could be expected at best only plays a subordinate role, as a background reaction, in the miniemulsion when ultrasound is used.

It can furthermore be regarded as being surprising that the enzymes which are used are not affected by the ultrasound impulses, or other shearing forces employed, such that they lose their functional capacity to an excessive degree. Precisely in the light of the fact that ultrasound generates microbubbles in the sonicated medium, which bubbles, in connection with a collapse, generate temperatures of up to 5000 K and pressures of up to 1000 bar, the advantageous employment of compounds which are as fragile as enzymes must appear to be extremely surprising.

The concept of using miniemulsions for preparing optically active, low molecular weight molecules enzymatically has generally been unknown to date. It is only the implementation of an enzymic polymerization of lactones in miniemulsions (ref. see above which has thus far been described. In the enzymic transformations for preparing optically active organic compounds, the procedure according to the invention makes it possible to achieve reaction times which are shorter, and/or substrate quantities employed which are higher, as compared with conventional methods. That this would be the case was in no way obvious against the background of the prior art at the time of the invention.

EXAMPLES

Example 1 (=Comparative Example)

Lipase-catalysed Enantioselective Hydrolysis of Racemic β-aminoacid Esters in a Two-Phase System Having a Substrate Concentration of 242 g/l 80 ml of water are initially introduced and 1.45 g of Amano lipase PS (*Pseudomas cepacia*; obtained through Amano Enzymes, Inc.) are added to it. The undissolved solid is then filtered off. 80 ml of methyl tert-butyl ether (MTBE), as organic solvent component, is added to the aqueous enzyme solution which results as the filtrate. An automatic pH stat is used to adjust the two-phase system which is formed to pH 8.2, and to keep it constant at this pH, by adding 1M sodium hydroxide solution (obtained through Merck). On reaching a temperature of 20° C., 39 g of the racemic compound n-propyl rac-3-amino-3-phenylpropionate are then added and the reaction is started.

The reaction time is 18 hours, during which a white precipitate, comprising the desired product (S)-3-amino-3-phenylpropionic acid, accrues. 160 ml of acetone are added to complete the precipitation and the mixture is subsequently stirred for 45 min. The solid is filtered off and washed with a little acetone.

A conversion of 13.9% is initially observed after 1 hour. A conversion of approx. 50% is achieved after a reaction time of 15 hours. The product which is isolated after working up has an ee value of >99% with the yield being 41%.

Example 2

Lipase-catalysed Enantioselective Hydrolysis of Racemic β-aminoacid Esters in a Miniemulsion Having a Substrate Concentration of 242 g/l 40 ml of surfactant solution are initially introduced and 1.45 g of Amano Lipase PS (*Pseudomas cepacia*; obtained through Amano Enzymes, Inc.) are added to it. The undissolved solid is then filtered off.

In each case one third of the propyl ester to be employed (39 g in all) and one third of the hexadecane (in all 1.638 g) and in each case 40 ml of a 1% solution of surfactant are admixed and stirred using a magnetic stirrer. These three emulsions are now in each case treated for 4 min at 200 W using an ultrasonic probe.

The filtrate is combined with the three miniemulsions and an automatic pH stat is used to adjust the mixture to pH 8.2, and to keep it constant at this pH, by adding 1M sodium hydroxide solution (obtained through Merck). The reaction temperature is 20° C. and the reaction time is 17 hours, during which a white precipitate, comprising the desired product (S)-3-amino-3-phenylpropionic acid, accrues. 160 ml of acetone are added to complete the precipitation and the mixture is subsequently stirred for 45 min. The solid is filtered off and washed with a little acetone.

A conversion of 17.5% is initially observed after 1 hour. A conversion of approx. 49% is achieved after a reaction time of 6 hours. The product which is isolated after working up has an ee value of >99% with the yield being 41%.

Example 3

Lipase-catalysed Enantioselective Hydrolysis of Racemic β-aminoacid Esters in a Miniemulsion Having a Substrate Concentration of 484 g/l 40 ml of surfactant solution are initially introduced and 1.21 g of Amano Lipase PS (*Pseudomas cepacia*; obtained through Amano Enzymes, Inc.) are added to it. The undissolved solid is then filtered off.

In each case one third of the propyl ester to be employed (in all 65.21 g) and one third of the hexadecane (in all 1.369 g) and in each case 32 ml of a 1% solution of surfactant are admixed and stirred using a magnetic stirrer. These three emulsions are now in each case treated for 4 min at 200 W using an ultrasonic probe.

The filtrate is combined with the three miniemulsions and an automatic pH stat is used to adjust the mixture to pH 8.2, and to keep it constant at this pH, by adding 1M sodium hydroxide solution (obtained through Merck). The reaction temperature is 20° C. and the reaction time is 18 hours, during which a white precipitate, comprising the desired product (S)-3-amino-3-phenylpropionic acid, accrues. 160 ml of acetone are added to complete the precipitation and the mixture is subsequently stirred for 45 min. The solid is filtered off and washed with a little acetone and 100 ml of MTBE.

A conversion of 10.2% is initially observed after 1 hour. A conversion of approx. 45% is reached after a reaction time of 18 hours. The product which is isolated after working up has an ee value of >99% with the yield being 37%.

The invention claimed is:

1. In a process for the asymmetric enzymatic preparation of optically active organic compounds, the improvement comprising carrying out said enzymatic preparation in a miniemulsion with an enzyme that uses a racemic amino acid ester as a substrate.

2. The improvement of claim 1, wherein said miniemulsion comprises hydrophobic droplets in an aqueous medium.

3. The improvement of claim 2, wherein said hydrophobic droplets have a mean diameter of 20-1000 nm.

4. The improvement of claim 3, wherein said miniemulsion further comprises a surfactant.

5. The improvement of claim 4, wherein said surfactant is non-ionic.

6. The improvement of claim 5, wherein said surfactant is "LUTENSOL" AT 50.

7. The improvement of claim 3, wherein said hydrophobic droplets are stabilized by adding an inert hydrophobic substance.

8. The improvement of claim 7, wherein said inert hydrophobic substance is n-hexadecane.

9. The improvement of claim 3, wherein said enzymatic preparation of optically active organic compounds is carried out using an enzyme selected from the group of consisting of an oxidoreductase, a hydrolase, an isomerase, a transferase and a lyase.

10. The improvement of claim 9, wherein said racemic amino acid ester is a β-amino acid ester.

11. The improvement of claim 9, wherein said racemic amino acid ester is n-propyl rac-3-amino-3-phenylpropionate.

12. The improvement of claim 9, wherein said substrate is present at a concentration of greater than 300 g/l.

13. The improvement of claim 12, wherein said substrate is present at a concentration of greater than 450 g/l.

14. The improvement of claim 3, wherein said enzymatic preparation of optically active organic compounds is carried out using at least one enzyme that is provided by a microorganism in said microemulsion.

15. The improvement of claim 14, wherein said enzyme is selected from the group of consisting of an oxidoreductase, a hydrolase, an isomerase, a transferase and a lyase.

16. The improvement of claim 1, wherein said miniemulsion comprises:
   a) a continuous aqueous phase;
   b) a discontinuous hydrophobic phase in the form of droplets;
   c) a stereoselective enzyme which is involved in the asymmetric preparation of an organic compound, or a microorganism which comprises this enzyme,
   d) a surfactant,
   e) a hydrophobic substance which stabilizes said droplets and
   f) a prochiral or racemic or enantiomerically enriched organic compound which is converted by said stereoselective enzyme and/or a reaction product of this compound.

17. The improvement of claim 16, wherein said droplets have a mean diameter of 20-1000 nm.

18. The improvement of claim 17, wherein said stereoselective enzyme is selected from the group of consisting of an oxidoreductase, a hydrolase, an isomerase, a transferase and a lyase.

* * * * *